United States Patent [19]

Allen et al.

[11] Patent Number: 5,074,154
[45] Date of Patent: Dec. 24, 1991

[54] FLUID SAMPLING PUMP

[75] Inventors: Paul V. Allen; Spencer M. Nimberger; Robert L. Ward, all of Houston, Tex.

[73] Assignee: Precision General Inc., Houston, Tex.

[21] Appl. No.: 496,368

[22] Filed: Mar. 20, 1990

[51] Int. Cl.$^5$ .............................................. G01N 1/14
[52] U.S. Cl. ................................. 73/864.34; 417/553
[58] Field of Search ........... 73/863.83, 864.34, 864.35; 417/549, 552, 553

[56] References Cited

U.S. PATENT DOCUMENTS

| 2,629,328 | 2/1953 | Ladd | 417/549 |
|---|---|---|---|
| 2,775,944 | 1/1957 | Ryder et al. | 417/549 |
| 4,172,670 | 10/1979 | Welker . | |
| 4,403,518 | 9/1983 | Welker . | |
| 4,440,032 | 4/1984 | Welker . | |
| 4,470,773 | 9/1984 | Welker . | |
| 4,525,127 | 6/1985 | Welker . | |
| 4,531,895 | 7/1985 | Zeck . | |
| 4,557,151 | 12/1985 | Welker . | |
| 4,628,750 | 12/1986 | Welker . | |
| 4,928,536 | 5/1990 | Welker | 73/863.83 |

FOREIGN PATENT DOCUMENTS 8912750 12/1989 World Int. Prop. O. .......... 417/552

OTHER PUBLICATIONS

Welker advertisement "WelkerStar Solar Powered Gas Sampler".

Primary Examiner—Robert Raevis

[57] ABSTRACT

A sampling pump is provided suitable for pumping a discrete quantity of either a liquid or a gas per pump stroke from a flow line to a sample vessel. An operator unit drives a piston within the pump bore, and controls the stroke of the piston and thus the quantity of fluid pumped per stroke. A balanced check valve mechanism controls flow from the pump bore to the pump outlet port, and is provided within and carried by the piston. Line pressure acts on the operator end of the piston to assist the operator in driving the piston during its power stroke. A manifold may be secured to the pump body, and has a flow path therein which is in communication with the inlet port to the pump bore. The pump may also be used for injection purposes to introduce a selected quantity of fluid to a high pressure line.

23 Claims, 3 Drawing Sheets

FLUID SAMPLING PUMP

BACKGROUND OF THE INVENTION

1. Field of the Invention

The present invention relates to pumps which deliver a preselected volume of fluid for each pump stroke and, more particularly, relates to sampling pumps of the type commonly used to intermittently withdraw sample hydrocarbon fluids from a pipeline and input those fluids to a sample vessel for subsequent analysis.

2. Description of the Background

Sampling pumps have been used for years to intermittently withdraw fluid samples from a hydrocarbon pipeline and input those samples to a suitable container for subsequent analysis. The price charged for hydrocarbons being transmitted through the pipeline is typically determined as a function of (a) the volume of the actual fluid transferred through the pipeline, and (b) the BTU content of sample fluid intermittently withdrawn from the pipeline. The sample fluid vessel is periodically transported to a laboratory for fluid analysis by any suitable instrument, such as a gas chromatograph. The accuracy of the sampling technique, i.e., the caloric or BTU value of the fluid sample in the vessel compared to the average BTU value of all the fluid transmitted through that pipeline, thus has a significant affect on the price paid for the transmitted fluid. Accordingly numerous attempts have been made and will continue to increase the reliability and accuracy of this sampling technique, while at the same time lowering the overall sampling costs.

One version of a sampling pump is disclosed in U.S. Pat. No. 4,403,518. U.S. Pat. No. 4,470,773 discloses a similar pump with a feature for breaking the vacuum in the pump which could otherwise be created by the retraction of the collection probe from the resilient plug. The prime mover for reciprocating the sampling pump piston is typically a diaphragm, which in turn is powered by a pressurized air source, as disclosed in U.S. Pat. Nos. 4,440,032 and 4,525,127. U.S. Pat. Nos. 4,557,151 discloses a sampling pump which also utilizes this type of prime mover, and further discloses a pressure balanced check valve external of the pump body. This check valve utilizes line pressure as a reference, and enables the pump to perform its desired function of transmitting a preselected fluid volume per stroke regardless of line pressure.

Most sampling pumps are primarily intended to pump either a liquid or a gas, but not both. Generally, gas sampling pumps typically transfer up to 0.04 cc of gas to the sample vessel per pump stroke, while liquid sampling pumps typically operate in the range of from 0.5 cc to 3 cc of fluid per pump stroke. Since the gas sampling pump takes "small bites," precise displacement of the pump piston must be controlled. A pump intended for sampling a typical substantially incompressible liquid, on the other hand, is usually provided with a large diameter pump piston, so that the stroke of the piston and thus the size of the pump may be maintained within a practical range. A representative liquid sampling pump is disclosed in U.S. Pat. No. 4,172,670, while a gas sampling pump is described in U.S. Pat. No. 4,531,895. Sampling pumps designed to pump gases are promoted as having little or no pump "dead volume" which adversely affects sampling reliability. All the gas drawn into the sampling pump during each stroke is transferred from the pump to the sample vessel, and no substantial amount of gas remains in the pump body when the piston is in its most downward position adjacent to the pump inlet. A combined pump and sample vessel is disclosed in U.S. Pat. No. 4,628,750.

U.S. Pat. No. 4,531,895 referenced above discloses a sampling pump which again utilizes a diaphragm as the driver for the pump piston, although the balanced check valve concept is obtained by a seal, valve, and valve seat each radially within of the sampling pump body. This patent also teaches a cylindrical plunger and a disc inlet valve, each having a snug fit within the cylindrical piston-receiving bore in the pump body. Due to reduced material and manufacturing costs, a sampling pump with an internal balanced check valve as disclosed in the '895 patent is generally preferred over a pump with a balanced check valve mechanism external of the pump body.

The sampling pump manufactured according to the '895 patent has several disadvantages which have limited its acceptance in the industry. In order to keep the size and cost of the pump within acceptable limits, the piston is relatively small, in part because the balanced check valve mechanism is positioned radially between the piston and the pump body. Accordingly the pump is primarily intended as a gas sampling pump, and is generally not considered acceptable for pumping the significantly larger fluid volume per pump stroke which is customarily required for sampling liquids.

In the design of the sampling pump as disclosed in the '895 patent, the balanced check valve seal is stroked by the piston during its downward and upward stroke, thereby wearing the seal. Moreover, the return or upstroke of the piston tends to unseat this check valve seal, which under certain conditions may allow fluid collected in the sample vessel to flow back into the pump, thereby destroying the integrity of the sample. Also, the gas inlet seal according to this design may lift off its seat during the pump return stroke, which then decreases the life and reliability of this seal.

Users of sampling pumps are justifiably concerned that filtering devices between the process line and the sampling pump may alter the composition of sampled fluid compared to the process line fluid. A pressure drop across such a filter provided in the "hot loop" of fluid upstream from the pump inlet port may adversely affect sampling reliability. An effective hot-loop filter would encounter significant plugging problems, and thus would significantly increase maintenance costs. Due to these concerns, process line fluid is typically not filtered, and particles in the process line which pass into the sampling pump have long had an adverse affect on pump reliability.

The operator for reciprocating a sampling pump piston must be sized sufficiently large to stroke the piston during its power stroke, thereby expelling sample fluid from the pump and into the sample vessel. The pressure of the fluid in the sample vessel may either be nominal or considerable, and may be less than or greater than the line pressure of the hydrocarbons or other fluid being transmitted through the pipeline. The cost of a large operator for stroking the sampling pump piston represents a significant factor in the manufacturing costs of the sampling pump, while the size of the required operator may result in significantly increased installation and repair costs.

Certain types of injection pumps are structurally and operationally similar to a sampling pump. The present invention thus also relates to injection pumps of the type utilized to inject a specific quantity of low pressure fluid into a high pressure pipeline. In an exemplary use of an injection pump, an oderizer is input to a high pressure natural gas line for leak detection. As is the case for sampling pumps, both the quantity of fluid pumped per stroke and the time interval between successive pump strokes is selectively adjustable. Although the pump according to present invention is primarily described hereafter as a sampling pump useful for sampling purposes previously described, it should be understood that the same pump may be referred to as an injection pump when installed in a system for fluid injection purposes.

The disadvantages of the prior art are overcome by the present invention, and an improved sampling pump is hereinafter disclosed. The pump of the present invention is suitable for reliably withdrawing various sample hydrocarbon fluids from a pipeline at various line pressures and inputting those fluids to a desired sample vessel.

SUMMARY OF THE INVENTION

The sampling pump is provided with a large diameter piston capable of pumping a discrete yet small volume of gas during each piston stroke. The stroke of the piston is readily adjustable, and the same sampling pump is capable of pumping a correspondingly discrete yet significantly larger quantity of fluid during the adjusted longer stroke. Accordingly, both manufacturing and servicing costs can be reduced according to the present invention, since one pump may more frequently be utilized for pumping either various gases or various liquids from respective pipelines to their associated sample vessels.

Line pressure is utilized to obtain the balanced check valve feature for the pump, although this same line pressure is intentionally input to act on the top of the piston. Line pressure accordingly assists the operator in driving the piston during the pump power stroke. This feature allows the operator to be downsized, resulting in the benefits previously noted. A central operator rod connects the piston to the pump operator, which optionally may be a spring biased piston. The pump is allowed to have no significant dead volume, so that the pump is suitable for sampling gases and highly compressible liquids. Two seals are provided radially between the pump body and the piston and axially between the pump inlet port and the pump outlet port to enhance pumping accuracy when line pressure approximates sample vessel pressure. A strainer is provided within a mainfold between the process line and the sampling pump to prohibit debris from entering the pump. The strainer does not extend across the entire cross-section of the hot loop path, so that all fluid continually flowing through the hot loop and returning to the process line is not cleaned. A purge line within the manifold has its inlet exterior of but closely adjacent the strainer to automatically clean the strainer during conventional purging of the sample vessel.

A balanced check valve mechanism is provided both internal of the pump body and internal of the cylindrical outer surface of the pump piston, i.e., the balanced check valve mechanism is within the piston. The check valve mechanism includes a check valve seal and a seat which both move with the stroking piston. The axially movable pressure responsive mechanism also within the piston comprises a central plunger and a compression member. When the line pressure is greater than pressure in the sample container, the central plunger engages and acts against the compression member to exert a balancing pressure on the seal in response to varying line pressure. The central plunger moves within the piston in sliding engagement with a Teflon seal to reduce frictional drag between the seal and the plunger. If pressure in the sample container is greater than line pressure, the central plunger is moved out of engagement with the compression member, and the higher sample container pressure acts directly on the compression member to exert the balancing pressure on the seal. The surface of the seal opposite the seat is continually exposed to pressure in the sample container to prevent any trapped pressure from forcing the seal to move with respect to the compression member toward the seat. Also, the application of sample container pressure to the check valve seal at a location axially opposite the seat substantially reduces erratic unseating of the seal. The check valve seal engages only the seat and the compression member during operation of the pump, and continually moves with the compression member to make or break its seal with the seat. Since the balanced check valve seal does not engage the exterior side walls of the piston either during the downward pump stroke or the upward return stroke, the seal is not worn by sliding engagement with the piston. The life of the balanced check valve seal is also enhanced since the seal is not drawn off its seat during the return stroke of the piston, thereby also avoiding the previously described problem associated with the by-pass of collected fluid from the sample vessel back through the pump to the line.

The inlet or suction check valve is constructed such that the surface of the inlet seal opposite the seat will not form a seal with the inlet check valve. One or more passageways through the inlet check valve thus act as a seal break between the inlet seal and the check valve. At high line pressure, these passageways prevent the inlet check valve seal from migrating radially outward between the seat and the inlet check valve and thereby erratically prohibiting the fluid from entering into the pump bore.

It is an object of the present invention to provide an improved pump capable of pumping discrete quantities of either a liquid or a gas from either a flow line or storage vessel into a sample vessel, or from a container vessel into a flow line.

It is an object of the present invention to provide a pump capable of displacing a small volume of a compressible gas utilizing a relatively short pump stroke, while also providing a relatively large diameter piston movable within the pump bore to displace a large quantity of liquid.

It is a further object of this invention to provide a highly reliable pump having a balanced check valve mechanism positioned within the pump piston.

It is another object of this invention to provide a balanced check valve sampling pump wherein line pressure assists the operator during the power stroke of the pump to expel fluid into the sample vessel.

It is a feature of the present invention that the balanced check valve mechanism include two independently movable components each provided within a comparatively large diameter piston of the sampling pump for exerting a balancing pressure on the seal.

Yet another feature of the invention is the utilization of a balanced check valve mechanism which includes a compression member to bias the seal against its seat when fluid pressure in the sampling vessel is higher than line pressure. A central plunger is axially moveable within the piston and is biased by a spring to engage its seat. The plunger acts against the compression member to transmit line pressure force to the seal and thereby maintain the balanced pressure feature for the sampling pump under high line pressure conditions.

It is another feature of the invention that the balanced check valve seal is not in sliding engagement with the outer sidewalls of the piston, thereby enhancing seal life.

It is also a feature of the invention that the volumetric range of fluid reliably displaced per pump stroke be adjustable by a multiple of more than 1:50, and preferably more than 1:100, so that the same pump may be reliably used to pump either a gas or a liquid from a product line to a sample vessel.

The accuracy of the fluid volume pumped per stroke is maintained when line pressure approximates sample vessel pressure by provided two seals between the pump inlet port and the pump outlet port, such that neither seal is responsive to both line pressure and sample vessel pressure.

It is another feature of the invention to provide a strainer within a manifold positioned between the pressure line and sampling pump which filters debris which otherwise would pass into the sampling pump. Fluid passing in the hot loop through the manifold and returning to the process line need not be filtered, and the strainer may be automatically cleaned by high velocity fluid passing by the strainer during the operation of purging each newly replaced sample vessel.

As yet a further feature of the invention, the compression member includes one or more through passageways for continually subjecting the check valve seal to sample vessel pressure at a position axially opposite the check valve seat.

Still another feature of the invention is that the pump inlet seal is prevented from sealing engagement with the inlet valve at a location axially opposite the inlet seat.

It is an advantage of the invention that a hydraulic powered piston may be employed as the operator for the sampling pump piston.

Still another advantage of this invention is that the pump piston and all components of the balanced check valve mechanism may be easily replaced as a module.

It is a further advantage of the invention that the pump is provided with a manifold connected directly to the pump body at a location adjacent the pump inlet port, thus minimizing the distance between the hot loop passageway and the inlet check valve.

These and further objects, features, and advantages of the present invention will become apparent from the following detailed description, wherein reference is made to the figures in the accompanying drawings.

BRIEF DESCRIPTIONS OF THE DRAWINGS

Figure 1:
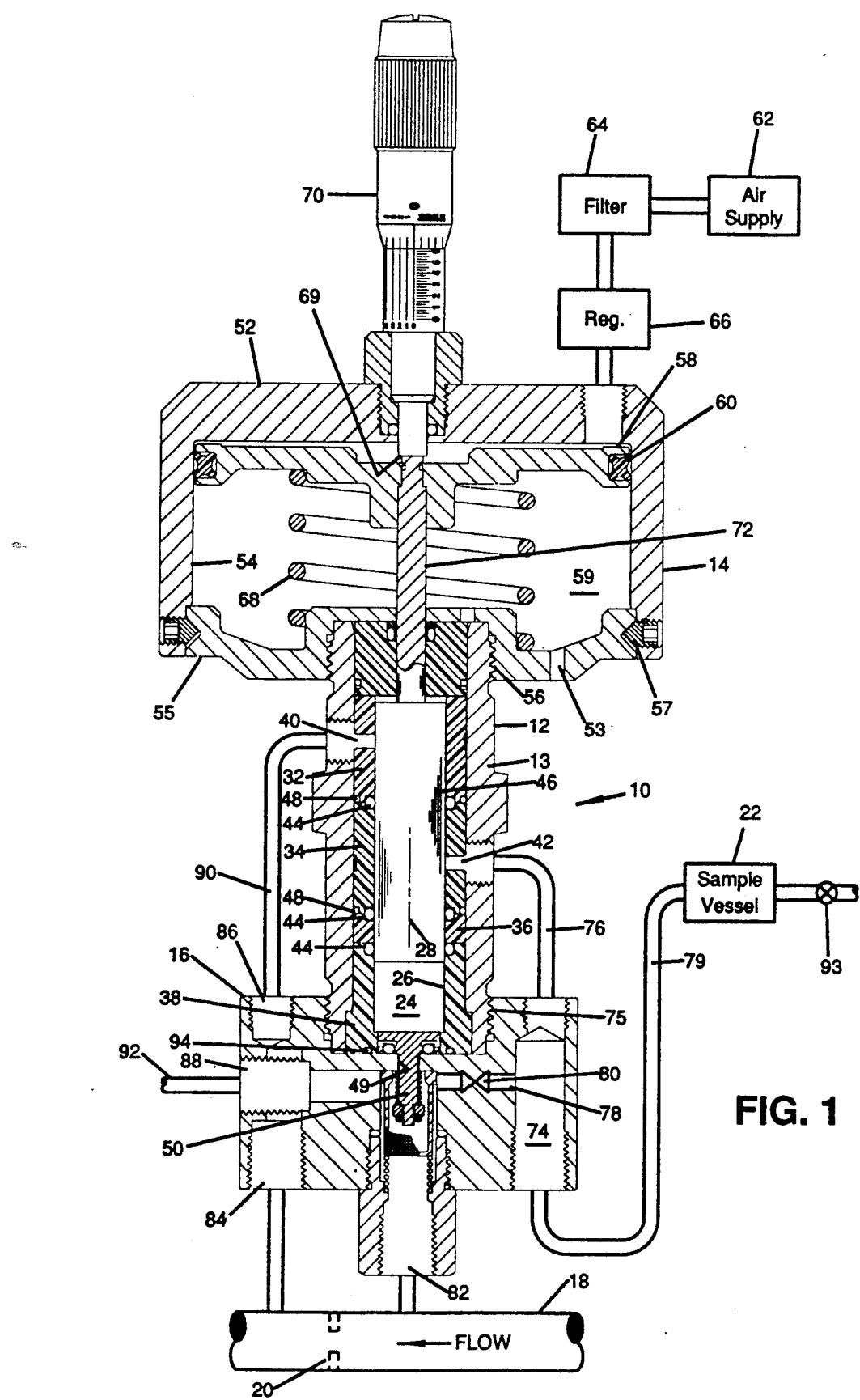
FIG. 1 is a pictorial view, partially in cross-section, of one embodiment of a fluid sampling pump according to the present invention in a typical application.
Figure 2:
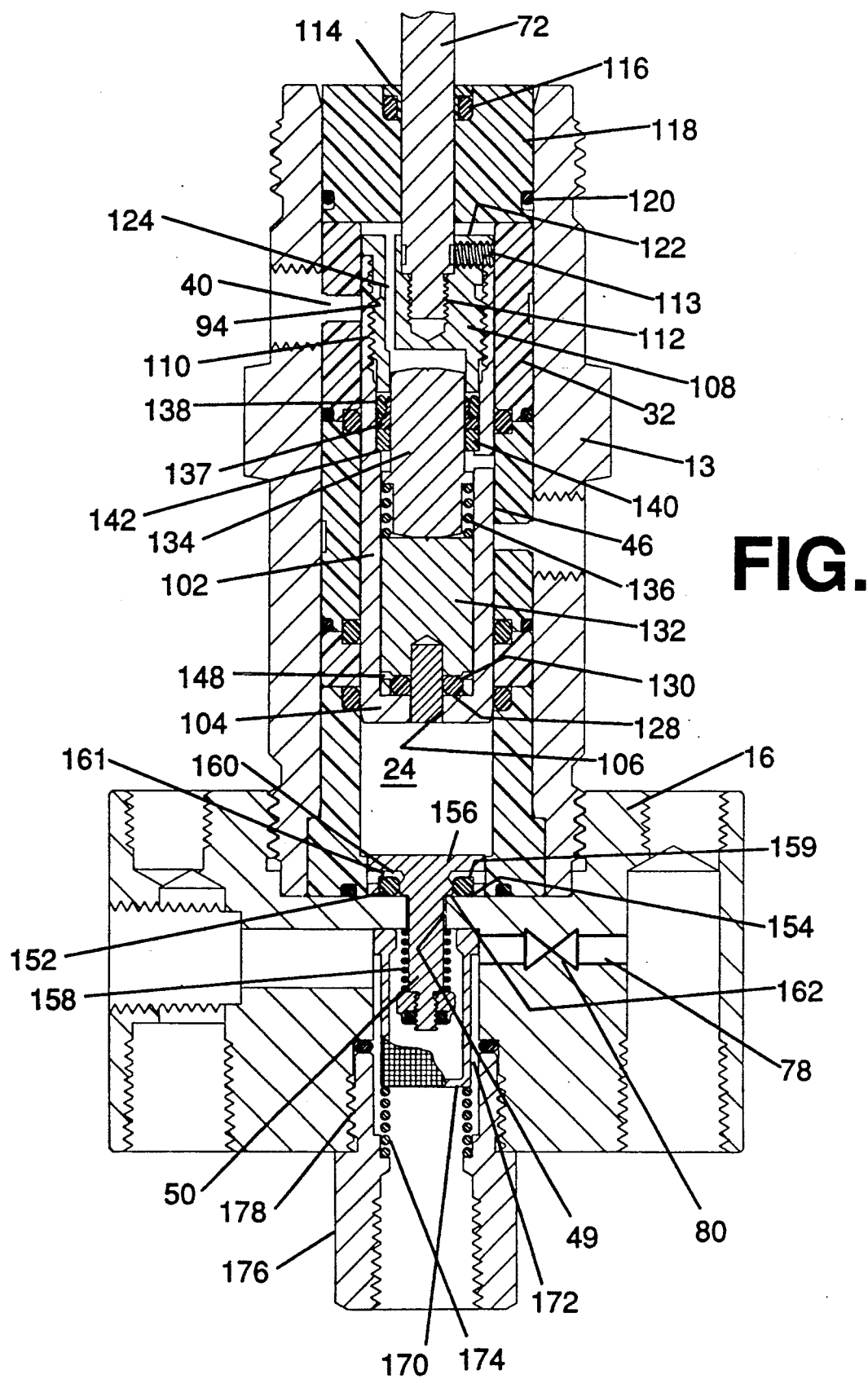
FIG. 2 is a detailed cross-sectional view of a portion of a sampling pump, with the pump piston shown in its retracted position and a strainer positioned within the manifold.
Figure 3:
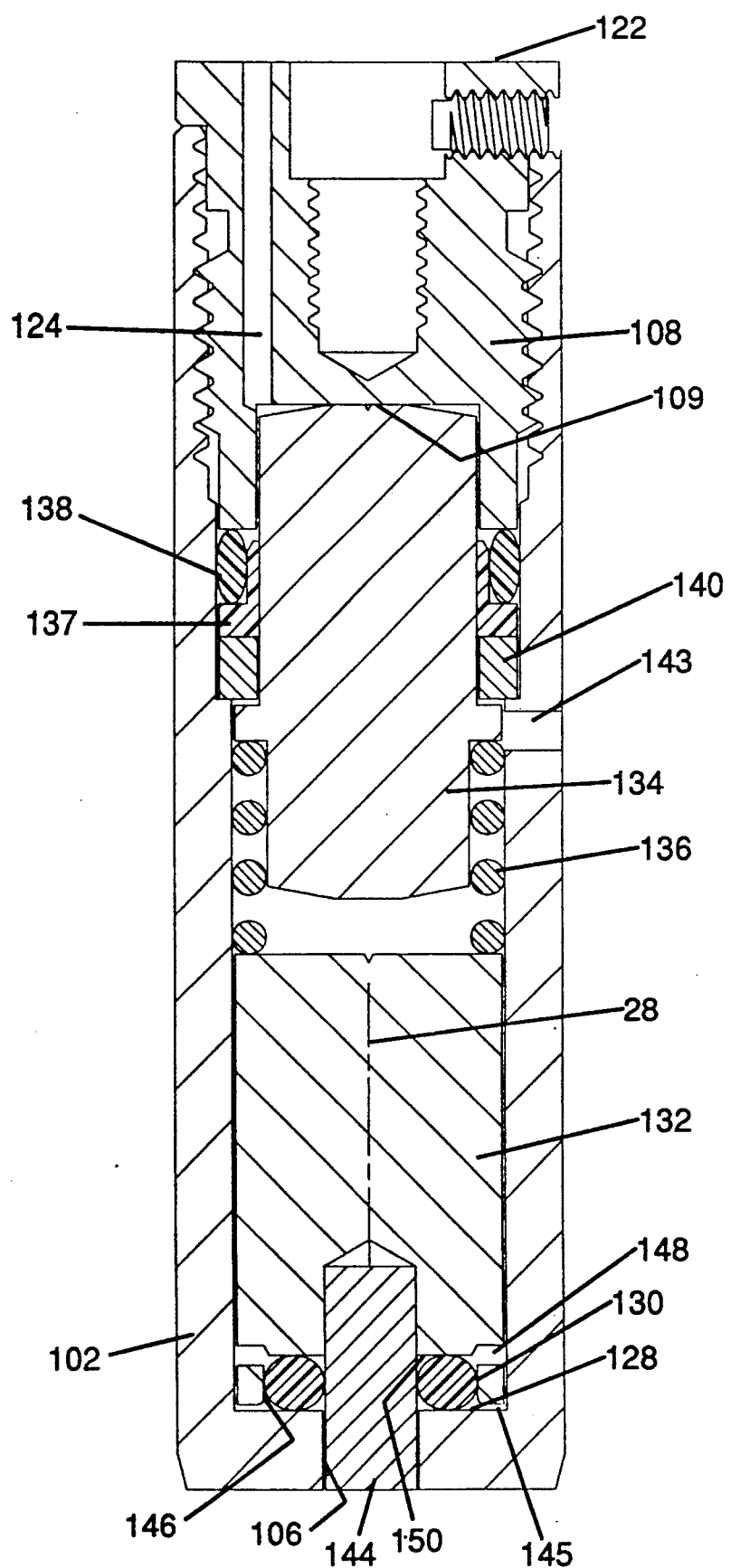

FIG. 3 a detailed cross-sectional view of the piston assembly generally shown in FIGS. 1 and 2, with the plunger out of engagement with the compression member.

DETAILED DESCRIPTION OF PREFERRED EMBODIMENTS

FIG. 1 depicts one embodiment of a sampling pump 10 according to the present invention. The pump 10 consists of a pump housing assembly 12, and a pump driving means or pump operator 14. The embodiment depicted includes a manifold 16 directly connected to the pump housing assembly, and will be discussed further below. The fluid to be sampled by the pump 10 is input to manifold 16 from pipeline 18, which typically has a flow restriction 20 for creating a differential pressure useful for determining the rate of fluid flow through the pipeline. Flow lines to and from the manifold 16, pump housing assembly 12 and pump operator are illustrated schematically in FIG. 1 for clarity, and the pump inlet and outlet ports are threaded for receiving conventional flow line fittings (not shown). Fluid flow through the manifold 16 is nominal compared to fluid flow through the restriction 20. Moreover, most fluid entering the manifold 16 exits the manifold and returns to line 18 downstream of the restriction 20. A very small percentage of the fluid passing through the line 18 is pumped by 10 to a sample vessel 22 for subsequent analysis.

The pump housing assembly 12 includes an exterior pump body 13 and a plurality of interior sleeve segments defining an inner bore 24 formed by a cylindrical interior surface 26 having a central axis 28. Bore 24 may be economically formed by the plurality of sleeve segments 32, 34, 36 and 38, although functionally the body 13 and sleeve segments perform as a unitary structure. The upper sleeve segment 32 includes a line pressure port 40, and engages sleeve segment 34, which in turn has a fluid sample outlet or discharge port 42. An annular groove in the end of each segment 32 and 34 is provided for housing an O-ring seal 44 which pressure isolates the line pressure port from the sample vessel. A pair of similar O-ring seals 44 are located above and below the pressure barrier sleeve segment 36, which is axially fixed between segment 34 and lower segment 38. Each seal 44 is thus positioned within a respective groove adjacent the ends of sleeve segments for both dynamic sealing with the piston 46 axially movable within the bore 24, and for static sealing between the sleeve segments. Additional static seals 48 provide a fluid-tight seal between the pump body 13 and the outer surface of the sleeve segments positioned therein.

Each of the seals 44 continually remains in sealing engagement between the pump sleeve segments and the piston 46 during the full stroke of the piston within the bore 24. Fluid flow from the flow line 18 into the pump bore 24 is regulated by the check valve assembly 50 which controls flow through the fluid sample inlet port 49. Each of the two seals 44 axially between the outlet port 42 and the inlet port 49 is only subjected to fluid pressure within either the outlet port 42 or the pump bore 24. Since neither seal 44 is subject to both pressure in the pump bore and sample vessel pressure, variations in the comparative strength of these pressure which occur during a pumping cycle do not cause axially opposing movements of these seals. By eliminating the "chucking action" which would otherwise occur if a single seal were utilized, the bite size of sample fluid per pump stroke is not significantly affected by such varying pressures.

The pump operator 14 includes an inverted bowl-shaped cylinder housing 52 having a cylindrical interior surface 54 with a central axis coaxial with 28. A lower adapter plate 55 is secured to 52 by set screws 57, and includes threads 56 for secured engagement with the housing assembly 12 and a pressure relief port 53. A piston 58 is axially moveable within the cylindrical chamber 59 of housing 52, and includes a perimeter seal 60 for sliding engagement with surface 54. Fluid pressure from air supply 62 may pass through filter 64 and regulator 66, and be input to the operator 14 to periodically drive the piston 58 toward the housing assembly 12 during the power stroke of the pump cycle. The release of air pressure to the operator 14 from 62 accordingly will allow the coil spring 68 to move the piston 58 away from the pump body assembly 12 during the pump return stroke. Connecting rod 72 is secured at one end to the operator piston 58, and at the other end to the pump piston 46. The stroke of the pump piston 46 may be set by a caliper mechanism 70, which provides an axially centered adjustable stop 69 for limiting upward movement of both the Operator piston 58 and the pump piston 46 connected therewith. The pump piston is thus stroked by the operator 14 within the inner bore 24 of the pump body 12 to input a selected quantity of fluid to the bore 24 with each upward or return stroke, and to pump the selected quantity of sample fluid to the vessel 22 with each pump downward or power stroke.

The operator 14 as shown in FIG. 1 has several advantages over an operator with a diaphragm as the prime mover. Operator reliability is increased by using a piston, which is not damaged as easily as a diaphragm. Moreover, the size of the operator, i.e. its physical diameter, may be reduced both because of the utilization of higher pressures from supply 62 than are normally recommended for a bladder, and because the pump piston is assisted during its pumping stroke by line pressure from supply line 18, as explained subsequently. The pump 10 may be intermittently actuated by air pressure from 62, and each cycle of the pump will input the preselected quantity of fluid from the pipeline 18 to the sample vessel 22. Further details with respect to sequencing of a sampling pump are disclosed in U.S. Pat. No. 4,531,895, which is incorporated by reference herein.

Manifold 16 is directly connected to the pump body by threads 75. Manifold 16 includes a fluid input port 82 and outlet ports 84, 86 and 88. A small quantity of fluid flows in a hot loop from line 18 into the manifold 16 via port 82 and out port 84 back to line 18. Port 86 establishes line pressure communication from line 18 to port 40 in the pump body via conduit 90. Line 92 is connected to port 88, and optionally may extend to the regulator 66 for powering operator 14. Seal 94 maintains fluid-tight communication between the lower sleeve segment 38 and the manifold 16. By directly connecting the manifold to the pump body, the number of leak points may be reduced. The manifold as shown in FIG. 1 enables the single fluid input line to the sampling pump and both the fluid output lines to the sampling vessel and back to the process line 18 to be connected to a lower face of the manifold, so that the manifold, pump body and operator may be easily enclosed for protection. The manifold desirably positions the "slip stream" of fluid continually flowing in the hot loop through the manifold to pass in close proximity to the fluid inlet to the sampling pump body. Use of the manifold 16 between the line 18 and the pump body minimizes installation costs, and provides a compact assembly with a fixed hot loop path closely adjacent the pump inlet.

Manifold cavity 74 connects to outlet port 42 in the pump body via conduit 76, and to sample vessel 22 via conduit 79, thereby providing a flow path from the pump to the sample vessel 22. Conduit 78 and purge valve 80 are integral to the manifold and connect inlet port 82 to manifold cavity 74. Purge valve 80 is normally closed during pump operation. When a filled sample vessel 22 is replaced with another vessel, both valves 80 and 93 may be opened to enable fluid from line 18 to purge conduit 79 and the new sample vessel of air or sample fluids from previous jobs. Once purged, purge valve 80 then valve 93 is closed. Fluid from line 18 at atmospheric pressure occupies the line 79 and the sample vessel, and the sampling operation as described in prior art patents may then be initiated.

Referring now to FIG. 2, the piston 46 comprises a sleeve-shaped outer body 102 having an integral end 104 with a cylindrical opening 106 therein. A piston end cap 108 is threadably connected at 110 to the operator end of the piston. Threads 112 connect rod 72 to the piston end cap, and set screw 113 rotationally locks the rod to the end cap. A top plug 118 is sealed with the rod 72 by a Teflon seal 114 biased into engagement with rod 72 by O-ring 116, while seal 120 provides a static seal between the body 13 and the plug 118. The pump body defines an annulus 94 between the internal surface of the sleeve segment 32 and the outer cylindrical surface of the pump piston 46, so that absence of seals between the top plug 118 and port 40 ensures that line pressure will pass through clearance 94 and continually act on the operator end 122 of the piston to assist the operator 14 during the downstroke of the piston. A flow path 124 in end cap 108 ensures that the same line pressure will be available to act on the check valve mechanism of the present invention, regardless of the position of the pump piston 46 within the body 13.

It is a significant feature of the invention that pressure in the flow line 18 (which is identical to pressure in port 40) is used to both pressure balance the outlet check valve mechanism and assist the operator unit 14 in driving the piston 46 during its downward or power stroke. Previous operators for the sampling pumps discussed earlier had to be sized to overcome the possibly high line pressure in pump bore 24, which significantly increased the cost of the operator. By continually enabling line pressure to act on the operator end 122 of the piston 46, the driving force required by the operator unit 14 is reduced. Moreover, the use of a fluid-powered piston 58 rather than a bladder enables a relatively small operator unit 14 to provide the required power stroke force, since higher pressure may be safely applied to the operator.

The balanced check valve mechanism is provided completely within and is thus carried by the piston 46. This mechanism includes O-ring seal 130 which seals against seat 128 on the body 102, compression member 132 which normally acts on seal 130 to bias the seal into sealing engagement with seat 128, plunger 134 and coil spring 136. Assuming sample vessel pressure is low, line pressure in port 40 passes through flow path 124 in end cap 108 and moves plunger 134 downward to compress spring 136 and engage compression member 132. Teflon seal 137 is supported on the piston 46, and is biased into fluid-tight sealing engagement with plunger 134 by O-ring 138. Stainless steel backup ring 140 is prevented from moving downward toward seal 130 by lip 142 on the piston body 102. The two-piece seal 137, 138 is thus substantially fixed axially on the piston 46 between the backup ring 140 and the lower end of the cap 108. During both downward axial movement of the plunger 134 in response to high line pressure or upward movement in response to high sample vessel pressure, the seal 137 results in a relatively low friction drag to minimize problems associated with "sticking" of the member 134. One of the advantages of the invention is that the pump piston and the balanced check valve components may be easily replaced as a module, thereby minimizing maintenance costs and reducing pump down time. Seal members 114 and 116 discussed above are functionally similar to 137 and 138, and are provided for low friction sealing between the top plug 118 of the pump body and the rod or stem 72.

FIG. 2 illustrates an inverted cup-shaped strainer 170 positioned in the slip stream within the manifold 16. The mouth of the strainer is held against the inlet port to the pump body, so that all fluid entering the pump bore 24 must first pass through the walls of the strainer. An annulus 172 is intentionally provided between the exterior cylindrical outer surface of the strainer and the flow path walls which define the slip stream, and most fluid entering the manifold flows back to the process line and is not filtered, thereby minimizing plugging problems. The strainer 170, which preferably is selected to filter particles in the 100 micron size or greater, is removably held in place by a coil spring 174 and a nipple 176 which is threaded at 178 to the manifold body 16. If required, the nipple 176, coil spring 174 and strainer 170 may thus be easily removed from the manifold for cleaning.

Required cleaning of the strainer 170 is substantially minimized since all fluid passing through the manifold is not strained. Moreover, the strainer 170 may be automatically cleaned by opening valve 80 during the previously described purging operation, which typically occurs prior to initiating sampling into a new vessel. Fluid passing through line 78 flows by the exterior of the strainer to perform the cleaning operation. By positioning the inlet for line 78 exterior of yet closely adjacent the strainer, and also closely adjacent the mouth of the strainer and thus the inlet to the pump body, the high-velocity purging fluid intentionally flows about the strainer to sweep particles from the strainer walls.

Referring to FIG. 3, the plunger 134 is independently moveable within the piston relative to the compression member 132, and is biased out of engagement with the member 132 by spring 136. The piston body 102 includes through port 143 which allows sample vessel or bottle pressure at outlet port 42 (see FIG. 1) to pass into the interior of piston 46 to act on the compression member 132. The lower end of compression member 132 is provided with an interior wall 146 which defines a cylindrical chamber for receiving the O-ring seal 130. The lower end of the compression member is also provided with a pin 144 secured thereto and occupying the cylindrical passageway 106 within the lower end of the piston body 102. The O-ring seal 130 thus radially engages to seal with both the interior cylindrical surface 146 of member 132 and the exterior cylindrical surface of the pin 144, and axially engages the end surface 150 of member 132. The seal 130 is thus supported on and moves axially together with the member 132 and the pin 144, to disengage or come off the seat 128 and thereby allow fluid to flow from the chamber 24 to the sample vessel 22 during the downstroke of the piston. Seat 128 on the piston body 102 preferably lies in a plane perpendicular to a central axis 28 of the bore. One or more drilled passageways 148 extend radially between the cylindrical chamber formed by the piston body 102 and the outer surface of the compression member 132.

The ring-shaped recess in the compression member 132 defined by the interior surface 146, the exterior surface of pin 144, and seal engaging surface 150 is thus substantially occupied by the elastomeric seal 130. The lower exterior surface of seal 130 engages and seals with seat 128, while its axially opposing upper surface contacts planar end surface 150 of the compression member. The one or more drilled passageway 148 extend radially between the ring-shaped recess and the exterior cylindrical surface of the compression member, and serve to vent any build-up of pressure between the O-ring 130 and the surface 150 which otherwise may tend to push the seal out of the recess. In addition, the drilled holes 148 substantially eliminate erratic releasing of the seal 130 from the seat 128 by continuously applying sample vessel or bottle pressure in port 42 to the upper exterior surface of the seal axially opposite the seat 128. Erratic releasing and unreliable performance of the seal 130, which was of particular concern when sample vessel pressure was high, has been avoided by providing the drilled holes 148. As shown in FIG. 3, the end surface 145 of compression member 132 normally does not engage or "bottom out" on seat surface 128, so that the pressure applied to force seal 130 toward seat 128 remains a function of the higher of the line pressure or the sample vessel pressure.

Referring again to FIG. 2, the inlet check valve assembly comprises O-ring seal 152 having a circular cross-sectional configuration, and seals against seat 154 formed on an exterior surface of the manifold 16. Valve member 156 is biased by spring 158 to force the O-ring 152 into sealing engagement with the seat. One or more drilled passageways 160 extend radially from the outer surface of the valve member 156 to a position radially inward of the O-ring seal 152, and prevent a portion of the surface of the seal 152 axially opposite the seat 154 from sealingly engaging the valve member.

The drilled holes 160 create a small amount of undesireable "dead space" and accordingly the diameter of the valve member 156 as well as the diameter and number of drilled holes 160 therein is minimized. This disadvantage is offset, however, by the substantial benefit of the drilled holes 160 in preventing a seal between the member 156 and the upper surface of the seal 152. Without the drilled holes 160, the pressure differential across the seal 152 as the valve member starts to move axially to break the seal tends to allow the seal to flow radially outward between the valve member 156 and the seat 154. This was a significant problem, particularly when pumping viscous liquids, which has been overcome by the incorporation of the drilled holes 160.

The inlet seal 152 has a lower exterior portion which seals against seat 154, and an opposing upper exterior portion which engages the surface 159 on the valve member. Seal 152 substantially fills a ring-shaped recess in the valve member 156, which is defined by a radially interior cylindrical surface 162, a radially exterior cylindrical surface 161, and the base surface or seal engaging surface 159 on the valve member. The radially outward exterior surface of the seal is in continued engagement with the surface 161 on the valve member. The passageways 160 provide an interruption in the otherwise planar surface 159, and release any pressure to the bore 24 which passes axially upward between the O-ring seal 152 and the radially inward exterior surface of the seal. Depending on the pressure differential across the seal 152, the seal according to the present invention can be initially "broke" either by having fluid pass under the seal 152 and between the seal and the seat 154, or by having fluid pass upwardly between the seal 152 and the cylindrical surface 162 of the valve member, then through the one or more drilled holes 160. Regardless of how the seal is broken, the drilled holes 160 substantially minimize sealing problems for the inlet check valve, and thereby increase the reliability of the sampling pump and reduce maintenance problems associated with the inlet check valve seal.

When the piston 46 strokes down, seal 152 prevents fluid in the bore 24 from flowing back to the manifold. The upstroke or return stroke of the piston 46 allows fluid in the manifold 16 to break or unseat the seal 152 from the seat 154. If line pressure is high, the initial seal break may occur by pressure passing between the seal 152 and the interior surface 162, then out the passageway 160. The high pressure differential across the seal 152 does not, however, force the seal radially outward between the end surface of the valve member and the seat. Under low line pressure, the seal will normally be broken by pressure lifting the valve member 156 and the seal axially off the seat 154 as the elastomeric seal is slightly compressed axially. Once the seal is broken, the valve member 156 will raise axially upward a small amount together with the O-ring seal 152 to allow line fluid to pass between the seal 152 and the seat 154 and fill the bore 24 below the piston. The equalization of pressure across the inlet check valve then allows the spring 158 to close the valve 156, forcing the seal 152 to re-engage the seat 154 and reseal the fluid sample inlet port.

Referring again to FIG. 2. the operation of a pump 10 is a described below for three possible situations: line pressure greater than bottle (sample vessel) pressure, line pressure less than bottle pressure, and line pressure approximately equal to bottle pressure. For each of these situations, it should be understood that a selected quantity of fluid pumped to the sample vessel 22 may be easily and accurately adjusted by caliper mechanism 70 (see FIG. 1) which controls the stroke of the piston 46 within the pump bore 24. The same pump 10 is capable of reliably pumping both liquids and gases under either relatively low or high line pressure. Accurate volumns of pumped fluid or "bites" per pump stroke have been reliably obtained for bite sizes as small as 0.05 cc, although the bite size for the same pump may be easily increased to approximately 3.0 cc, or to any incremental volume between these ranges as selectively determined by regulating caliper mechanism 70.

If line pressure is high, the pressure applied to plunger 134 compresses the spring 136 so that the plunger engages the compression member 132. Compression member 132 in turn presses downward on the O-ring seal 130. Because of the greater diameter of seal 137 compared to seal 130, the high line pressure in the bore 24 is prevented from passing by the seal 130. The pump is thus balanced against high line pressure to prevent the uncontrolled flow of fluid from a high pressure flow line through the pump and into a comparatively low pressure sample vessel. During the pump downward stroke, the pressure in bore 24 increases over line pressure to an amount sufficient to overcome the downward force of the plunger, and the compression member 132 and the pin 144 affixed thereto, as well as the plunger 134, move axially upward a slight amount, e.g., .010 inches. The seal 130 is carried by and thus moves axially with the compression member 132 to pass fluid from the pump bore, between the piston and the compression member 132, out port 42, and to the sample vessel, thereby completing the pumping cycle.

During the entire pumping cycle, the seal 130 is never stroked by the reciprocating piston since the balance check valve seal and seat are radially within and carried by the piston. The seal 130 continually moves with the compression member 132 to lift off the seat 128, although even this movement does not result in sliding frictional engagement between the seal and another member. Also, the high line pressure will assist the operator during the downward or power stroke of the piston 46 as fluid is pumped to the sample vessel 22.

If line pressure is markedly less than bottle pressure, the inlet check valve functions as described above, and line pressure still assists the operator in driving the piston during its downward stroke. In this case, however, bottle pressure at port 42 acts on the lower end of plunger 134 to drive the plunger upward to engage stop surface 109 (see FIG. 3) on the cap 108. The force required to move the plunger axially in response to a change in line pressure compared to bottle pressure is relatively low, and problems associated with sticking of the plunger are avoided by using the combination Teflon seal 137 and O-ring seal 138. High bottle pressure passes into the piston 46 through side port 143, then passes between the compression member 132 and piston member 102 and through the axial holes 148, to maintain the seal 130 in engagement with the seat 128. A pressure differential exists across the O-ring seal 130, since the lower exterior surface of the seal is exposed to the lower pressure in the pump bore 24. The pump is thus pressured balanced against high bottle pressure, since high pressure acting on the top of seal 130 prevents high pressure fluid from flowing past the seal 130 back to the lower line pressure within the bore 24. During the pump downward stroke, the pressure in bore 24 increases to a level greater than bottle pressure, and the seal 130 moves upward with the compression member 132 in response to this increased pressure to release fluid to the sample vessel. Drilled passageways 148 prevent any fluid build-up of pressure on the top side of the O-ring 130 which might otherwise force the O-ring out of its ring-shaped recess. Also, by applying pressure to the surface of the seal 130 axially opposite the seat, erratic unseating of the seal 130 from the seat 128 is avoided.

If line pressure is approximately equal to bottle pressure, the spring 136 provides the biasing force which is necessary to ensure a reliable operation of the outlet check valve assembly. In this situation, the low drag between the plunger and the seal 137 is particularly important. The spring 136 forces the plunger 134 upward, although the plunger 134 may rest in an intermediate position and engage neither the stop surface 109 nor the compression member 132, depending on the pressure differential and the spring force. In any event, at the end of the downward stroke of the piston 46, the spring biases the compression member 132 to act downwardly against the seal 130 to maintain sealed engagement with the seat 128 and thus prevent reverse flow back to the bore 24. The downward stroke of the piston will increase pressure in bore 24 and pass fluid to the sample vessel as previously described.

Standard materials may be used to fabricate the components for the sampling pump according to the present invention. Most components may be machined from aluminum, steel, or stainless steel, depending on the properties of the fluids intended to pass through the pump. The O-rings may be fabricated from various elastomeric materials, such as Viton, while the seals 114 and 137 are preferably fabricated from Teflon. The end plug 118 and sleeves 32, 34, 36, and 38 may be formed from a thermoplastic material, such as Delrin. The springs may be fabricated from standard materials, such as Inconel or stainless steel.

Various changes may be made to the specific embodiment disclosed above and shown in the accompanying drawings. The line pressure assist provided to move the pump piston downward during its power stroke allows various types of operators to provide the necessary driving force to pump fluids to the sample vessel. The manifold 16 is preferably secured to the fluid input end of the pump body, although the manifold could be eliminated and conventional fluid lines used to interconnect the pipeline 18 with the sampling pump.

The disclosure and description of the invention are thus illustrative and explanatory thereof, and various other changes in the size, shape, and materials, as well as the details of the illustrated construction, may be made within the scope of the appended claims and without departing from the spirit of the invention.

What is claimed is:

1. A fluid sampling pump for withdrawing pressurized sample fluid from a flow line and for pumping a preselected quantity of sample fluid with each pump driving stroke from the pump to a sample vessel, the sampling pump including a pump body defining a pump bore therein having a central axis, a piston slideably moveable within the pump bore and having a fluid inlet end and an opposing operator end, a fluid sample inlet port open to sample fluid in the flow line, a fluid sample outlet port for transmitting fluid from the pump bore to the sample vessel, and a line pressure port in fluid pressure communication between the pump bore and the pressurized sample fluid in the flow line, an inlet valve for selectively controlling sample fluid flow from the flow line through the fluid sample inlet port, an operator unit for periodically reciprocating the piston within the pump bore, and a controller for regulating the stroke of the piston within the pump bore and thereby the quantity of fluid pumped with each pump driving stroke, the fluid sampling pump further comprising:
    a balanced check valve seat radially within and carried by the piston;
    a balanced check valve seal radially within and carried by the piston for sealing engagement with the check valve seat to control fluid flow from the pump bore to the fluid sample outlet port;
    a compression member radially within and carried by the piston, the compression member being axially moveable within the piston in response to fluid pressure in the outlet port for biasing the balanced check valve seal toward the check valve seat when pressure in the outlet port is greater than pressure in the line pressure port; and
    a central plunger radially within and carried by the piston, the central plunger being axially moveable within the piston in response to pressure in the line pressure port for acting on the compression member and biasing the balanced check valve seal toward the check valve seat when pressure in the line pressure port is greater than pressure in the outlet port.

2. The fluid sampling pump as defined in claim 1, further comprising:
    the pump body having a pressure transmitting passageway for enabling fluid communication between the line pressure port and the operator end of the piston, such that sample fluid pressure in the flow line continually assists the operator unit in moving the piston toward the sample inlet port.

3. The fluid sampling pump as defined in claim 1, further comprising:
    a spring radially within and carried by the piston for biasing the compression member toward the balanced check valve seal.

4. The fluid sampling pump as defined in claim 1, further comprising:
    a first seal axially positioned between the fluid inlet port and the fluid outlet port for sealing engagement between the piston and the pump body, the first seal isolating fluid pressure in the pump bore between the piston and the fluid inlet from a second seal: and
    the second seal axially positioned between the first seal and the fluid outlet port for sealing engagement between the piston and the pump body, the second seal isolating fluid pressure in the fluid outlet port from the first seal.

5. The fluid sampling pump as defined in claim 1, wherein the inlet valve comprises:
    an inlet valve seat;
    an annular elastomeric seal having a first exterior surface for sealing engagement with the valve seat, a second exterior surface opposing the first surface, a radially outward exterior surface, and a radially inward exterior surface;
    a valve member having a first seal engaging surface for engaging the second surface of the elastomeric seal, and having a second seal engaging surface for engaging the radially outward exterior surface of the elastomeric seal;
    a spring for biasing the valve member to force the elastomeric seal toward the inlet valve seat; and
    the valve member including a fluid passageway therein open to the pump bore and extending to a position radially inward of the first seal engaging surface for passing sample fluid between the valve member and the radially inward exterior surface of the elastomeric seal and out the fluid passageway.

6. The fluid sampling pump as defined in claim 5, further comprising:
    the elastomeric seal is an O-ring seal having a substantially circular cross-sectional configuration; and
    the valve body includes a ring-shaped recess therein for receiving the O-ring seal, the recess being defined by an inner cylindrical surface, the second seal engaging surface being an outer cylindrical surface, and the first seal engaging surface extending radially between the inner and outer cylindrical surfaces.

7. The fluid sampling pump as defined in claim 1, further comprising:
    the balanced check valve seal having a first exterior surface for sealing engagement with the inlet valve seat and a second exterior surface axially opposing the first surface; and
    the compression member including (a) a ring-shaped recess therein for receiving the balanced check valve seal, the recess being defined by a radially inner surface in engagement with the balanced check valve seal, a radially outer surface in engagement with the balanced check valve seal, and a base surface extending radially between the inner and outer surfaces for engaging the second exterior surface of the balanced check valve seal, and (b) a fluid passageway within the compression member open to fluid pressure in the outlet port and extending into fluid communication with the second exterior surface of the balanced check valve seal to bias the balanced check valve seal toward the check valve seat.

8. The fluid sampling pump as defined in claim 7, wherein the balanced check valve seal is supported on and is axially moveable with the compression member to control fluid flow from the pump bore to the fluid sample outlet port.

9. The fluid sampling pump as defined in claim 7, wherein the balanced check valve seat engaged by the balanced check valve seal lies within a plane perpendicular to the central axis of the bore in the pump body.

10. The fluid sampling pump as defined in claim 1, further comprising:
   a radially inward plunger seal for dynamic sealing engagement with the axially moveable central plunger: and
   a radially outward plunger seal for static sealing engagement between the radially inward plunger seal and the piston and for biasing the radially inward plunger seal toward sealing engagement with the central plunger.

11. The fluid sample pump as defined in claim 1, wherein the operator unit comprises:
   an operator housing; and
   an operator piston slidable moveable with the operator housing and interconnected to the piston in the pump bore.

12. A fluid sampling pump as defined in claim 1, further comprising:
   a manifold body interconnected with the pump body, the manifold body having (a) a sample fluid inlet port open to sample fluid in the flow line, (b) a sample fluid outlet port in fluid communication with the outlet port in the pump body, (c) a sample fluid return port in fluid communication with the sample fluid inlet port and the flow line, (d) a line pressure outlet port passage in fluid communication with the sample fluid inlet port and the line pressure port in the pump body, (e) a through passageway for transmitting fluid from the outlet port in the pump body to the sample vessel, (f) a purge passageway for establishing fluid communication between the sample fluid inlet port in the manifold body and the through passageway, and (g) a valve for controlling fluid flow through the purge passageway.

13. A fluid sampling pump as defined in claim 12, further comprising:
   the manifold body including a seat for sealing engagement with the inlet valve: and
   a filter within the manifold for filtering fluid entering the pump bore.

14. A fluid sampling pump for pumping a selected quantity of sample fluid with each pump driving stroke from a flow line to a sample vessel, the sampling pump including a pump body defining a pump bore therein having a central axis, a fluid sample inlet port at a lower end of the pump bore and open to sample fluid in the flow line, a fluid sample outlet port for transmitting fluid from the pump bore to the sample vessel, and a line pressure port in fluid pressure communication between the pump bore and the pressurized sample fluid in the flow line, a piston slideably moveable within the pump bore and having a fluid inlet end and an opposing operator end, an operator unit for reciprocating the piston within the pump bore, and a rod connected at one end to the operator unit and at an opposing end to the piston for mechanically interconnecting the piston and the operator unit, the fluid sampling pump further comprising:
   a balanced check valve seat;
   a balanced check valve seal for sealing engagement with the check valve seat to control fluid flow from the pump bore to the fluid sample outlet port:
   a plunger axially moveable in response to pressure in the line pressure port for biasing the balanced check valve seal toward the check valve seat; and
   the pump body having a pressure transmitting passageway for continually maintaining fluid communication between the line pressure port and the operator end of the piston, such that sample fluid pressure in the flow line assists the operator unit in moving the piston toward the sample inlet port.

15. The fluid sampling pump as defined in claim 14, wherein the operator unit comprises:
   an operator housing;
   an operator piston slidable moveable within the operator housing and interconnected to the rod.

16. The fluid sampling pump as defined in claim 15, further comprising:
   a spring acting upon the operator piston for biasing the piston within the pump bore axially away from the fluid sample inlet port.

17. The fluid sampling pump as defined in claim 14, further comprising:
   a first seal axially positioned between the fluid inlet port and the fluid outlet port for sealing engagement between the piston and the pump body, the first seal isolating fluid pressure in the pump bore between the piston and the fluid inlet form a second seal: and
   the second seal axially positioned between the first seal and the fluid outlet port for sealing engagement between the piston and the pump body, the second seal isolating fluid pressure in the fluid outlet port from the first seal.

18. The fluid sampling pump as defined in claim 14, wherein the balanced check valve seat, the balanced check valve seal, and the plunger are each positioned radially within and are carried by the piston.

19. A method of operating a fluid sampling pump to withdraw pressurized sample fluid from a flow line and pump a preselected quantity of sample fluid with each pump driving stroke from the pump to a sample vessel, the sampling pump including a pump body defining a pump bore therein having a central axis, a fluid sample inlet port open to sample fluid in the flow line, a fluid sample outlet port for transmitting fluid from the pump bore to the sample vessel, and a line pressure port in fluid pressure communication between the pump bore and the pressurized sample fluid in the flow line, an inlet valve for selectively controlling sample fluid flow from the flow line through the fluid sample inlet port, a piston slideably moveable within the pump bore and having a fluid inlet end and an opposing operator end, and an operator unit for reciprocating the piston within the pump bore, the method comprising:

forming an outlet check valve seat radially within and carried by the piston:

positioning an outlet check valve seal member radially within and carried by the piston for sealing engagement with the outlet check valve seat to control fluid flow from the pump bore to the fluid sample outlet port;

positioning a plunger radially within and carried by the piston, the plunger being axially moveable within the piston in response to pressure in the line pressure port to bias the check valve seal member toward the check valve seat when pressure into the line pressure port is greater than pressure in the outlet port:

positioning a compression member radially within and carried by the piston between the plunger and the outlet check valve seal member, the compression member being axially movable within the piston in response to pressure in the outlet port to bias the check valve seal member toward the check valve seat when pressure in the outlet port is greater than pressure in the line pressure port; and maintaining fluid communication between the line pressure port and the operator end of the piston, such that sample fluid pressure in the flow line continually assists the operator unit in moving the piston toward the sample inlet port.

20. The method as defined in claim 19, further comprising:

positioning a spring within the piston for biasing the compression member toward the balanced check valve seat.

21. The method as defined in claim 19, further comprising:

supporting the balanced check valve seal member on the compression member such that the compression member and balanced check valve seal member move axially together within the piston to control fluid flow to the fluid sample outlet port.

22. The method as defined in claim 19, further comprising:

forming a ring-shaped recess within the compression member for receiving the balanced check valve seal member, the recess being defined by a radially inner surface and a radially outer surface each normally in sealing engagement with the balanced check valve seal member, and a base surface extending between the inner and outer surfaces; and maintaining fluid pressure communication between the outlet port and an exterior surface of the balanced check valve seal member axially opposite the check valve seat.

23. The method as defined in claim 19, further comprising:

axially positioning a first seal between the fluid inlet port and the fluid outlet port for sealing engagement between the piston and the pump body; and axially positioning a second seal between the first seal and the fluid outlet port for sealing engagement between the piston and the pump body, such that the first seal isolates the second seal from fluid pressure in the pump bore, and the second seal isolates the first seal from fluid pressure in the fluid outlet port.

* * * * *